United States Patent
Choi et al.

(10) Patent No.: US 6,383,379 B1
(45) Date of Patent: May 7, 2002

(54) METHOD OF PREPARING A MICROBIAL CULTURE FOR WASTEWATER TREATMENT

(75) Inventors: Ki-Seung Choi, Anyang; Jin-Man Kim, Suwon; Myung-Ho Cho, Suwon; Seung-Hwan Kim, Suwon; Jeong-Ho Park, Suwon, all of (KR)

(73) Assignee: SK Chemicals (KR)

( * ) Notice: Subject to any disclaimer, the term of this patent is extended or adjusted under 35 U.S.C. 154(b) by 0 days.

(21) Appl. No.: 09/529,071
(22) PCT Filed: Oct. 7, 1998
(86) PCT No.: PCT/KR98/00305
  § 371 Date: Jun. 19, 2000
  § 102(e) Date: Jun. 19, 2000
(87) PCT Pub. No.: WO99/18037
  PCT Pub. Date: Apr. 15, 1999

(30) Foreign Application Priority Data

Oct. 6, 1997 (KR) .......................... 97/51254

(51) Int. Cl.[7] .................................. B01D 1/00
(52) U.S. Cl. ................ 210/195.3; 210/202; 210/205; 210/610; 210/625
(58) Field of Search .............. 210/195.1, 195.3, 210/194, 202, 205, 209, 259, 607, 610, 611, 625

(56) References Cited

U.S. PATENT DOCUMENTS

| | | | | |
|---|---|---|---|---|
| 2,562,510 A | * | 7/1951 | Schlenz | 210/610 |
| 4,705,633 A | * | 11/1987 | Bogusch | 210/610 |
| 4,772,396 A | * | 9/1988 | Voyt | 210/610 |
| 4,882,059 A | * | 11/1989 | Wong et al. | 210/610 |
| 5,171,687 A | * | 12/1992 | Moller et al. | 210/610 |
| 5,288,405 A | * | 2/1994 | Lamb | 210/195.1 |
| 5,376,275 A | | 12/1994 | Raper | 210/605 |
| 5,531,898 A | * | 7/1996 | Wickham | 210/611 |
| 5,578,210 A | | 11/1996 | Klecka | 210/610 |
| 5,840,182 A | * | 11/1998 | Lucido et al. | 210/202 |
| 5,976,375 A | * | 11/1999 | Dorica et al. | 210/625 |

FOREIGN PATENT DOCUMENTS

JP 59-52595 * 3/1984

OTHER PUBLICATIONS

Abstract of Japan 59–042893.
Abstract of Japan JP8182493.
Abstract of Japan JP8197086.
Abstract of Soviet Union SU 1752727 A.

* cited by examiner

Primary Examiner—Christopher Upton
(74) Attorney, Agent, or Firm—Baker Botts LLP

(57) ABSTRACT

A method of preparing a microbial culture for wastewater treatment comprising the steps of supplying an aerated material derived from an aeration tank (13) to a bioreactor (17) and cultivating a microorganism existing in the aerated material by adding a culture having a relatively long preservation time and a large number of effective microorganisms.

2 Claims, 4 Drawing Sheets

METHOD OF PREPARING A MICROBIAL CULTURE FOR WASTEWATER TREATMENT

CROSS REFERENCE TO RELATED APPLICATION

This application is based on application No. 97-51254 filed in the Korea Industrial Property Office on Oct. 6, 1997, the content of which is incorporated hereinto by reference.

BACKGROUND OF THE INVENTION (a) Field of the Invention

The present invention relates to a method of preparing a microbial culture for wastewater treatment, more particularly, to a method of preparing a microbial culture comprising step of cultivating a microorganism existing in an aeration tank of a wastewater treatment plant.

(b) Description of the Related Art

In a biological wastewater treatment method, many organic materials in wastewater can be decomposed, detoxified and removed by a microorganism. The biological method is classified into an aerobic treatment and anaerobic treatment. The aerobic treatment is classified into an activated sludge process, trickling filter process, rotating biological contactor process, oxidization pond process. The anaerobic treatment is classified into an anaerobic digestion process and septic tank process.

In the activated sludge process, many organic materials in wastewater can be decomposed by an aerobic metabolism of a microorganism.

FIG. 2 shows the conventional activated sludge process. An influent is fed into a primary settling tank (11). A volume and pH of the influent (raw sewage) is controlled in the primary settling tank (11). A solid substance and suspended solid (SS) substance are removed from the raw sewage in the primary settling tank (11). And then, the sewage is fed into an aeration tank (13) continuously. In the aeration tank (13), many organic materials are oxidized and decomposed by aerating with an aerobic microorganism. And then, a mixture of the aeration tank (13) is fed into a secondary settling tank (15) continuously. Sludge floc in the mixture are settled and separated in the secondary settling tank (15). A part of the settled sludge is resupplied to the aeration tank (13) through a return sludge line (19) and the other part of settled sludge is dehydrated and disposed as a waste sludge. A supernatant of the secondary settling tank (15) is sanitized and discharged. The aeration tank playing an important role in the activated sludge process is a concrete construct and contains an activated sludge generally.

A microbial culture for wastewater treatment is a microorganism goods to promote a decomposition of various materials and to decrease BOD, COD and SS concentration, being added to the aeration tank.

The microbial culture for wastewater treatment is classified into a solid type formulation and a liquid type formulation. The solid type microbial culture for wastewater treatment may be prepared by enrichment cultivating a microorganism, inoculating the microorganism to a cereal medium, cultivating, hot-drying and crushing. Otherwise, the solid type microbial culture may be prepared by cultivating an inoculum in a liquid medium, freeze drying the cultured material and mixing the freeze dried material with a rice straw, rice bran, sawdust, fallen leaves or cereal. In a different way, the solid type microbial culture may be prepared by cultivating an inoculum in a liquid medium, adding a surfactant to the liquid medium and spray drying the cultured material.

The liquid type microbial culture for wastewater treatment may be prepared by enrichment cultivating a microorganism in a liquid medium, adding a silicon oil and nonionic surfactant to the liquid medium.

The solid type microbial culture has a relatively long preservation time. However, it has a relatively long activation time. The liquid type microbial culture has a relatively short activation time. However, it has a relatively short preservation time.

To solve the problem of the solid type microbial culture, Korean Patent Laid-Open Publication No. 95-26824 discloses a method of preparing a microbial culture for wastewater treatment using a microorganism separated from soil and adding a sludge as a promoter for the microbial culture.

Korean Patent Laid-Open Publication No. 96-14334 discloses a method of preparing a microbial culture for wastewater treatment adding a skim milk and glutamate to a medium and freeze drying.

To solve the problem of the liquid type microbial culture, Korean Patent Laid-Open Publication No. 96-22289 and No. 96-22288 disclose a method of preparing a microbial culture for wastewater treatment adding a nonionic surfactant and glycerol to a liquid medium and spray drying.

Korean Patent Laid-Open Publication No. 94-6931 discloses a microbial culture for wastewater treatment comprising propionate as a microbial growth inhibitor. The microbial culture has a relatively long preservation time. However, the microbial culture has a relatively low activation.

PCT application publication No. WO 96/15992 discloses a method of treating wastewater comprising steps of adding an aerobic microorganism and an anaerobic microorganism to a fermenter. This method does not generate any offensive odor, toxic gas and harmful substance. An object of the invention is to remove a harmful gas from sewage by using microorganisms separated from nature, not to cultivate microorganisms in the fermenter. This invention has a problem that microorganisms require a relatively long time to adapt to a sludge.

U.S. Pat. No. 5,376,275 discloses a method of treating wastewater comprising steps of fermenting a sewage sludge component for a period of at least 15 days under conditions to maximize the formation of soluble carbonaceous substrates in the sludge component, contacting the fermented sludge component with influent sewage to form a conditioned sewage, the conditioned sewage containing soluble carbonaceous substrates elutriated from the fermented sludge component, and supplying the conditioned sewage to the activated sludge treatment plant. The invention has a relatively long treating time of 15–60 days.

SUMMARY OF THE INVENTION

It is an object of the present invention to provide a method of preparing a microbial culture for wastewater treatment having a relatively long preservation time.

It is another object to provide a method of preparing a microbial culture for wastewater treatment having a lot of effective microorganisms to decompose an organic material in the wastewater.

In order to achieve these objects, the present invention provides a method of preparing a microbial culture for wastewater treatment comprising the steps of supplying an aerated material derived from an aeration tank to a bioreactor and cultivating a microorganism existing in the aerated material by adding a culture medium to the bioreactor.

The present invention provides a wastewater treatment plant comprising: a primary settling tank for removing a solid substance and a suspended solid substance from a raw sewage; an aeration tank for decomposing an organic material in a raw sewage by aerating the raw sewage with a microorganism, the aeration tank being linked to the primary settling tank; a bioreactor linked to the aeration tank, the bioreactor being supplied with an aerated material from the aeration tank and a culture medium, preparing a microbial culture by mixing the aerated material with the culture medium, and supplying the microbial culture to the aeration tank; and a secondary settling tank for settling a sludge floc supplied from the aeration tank, the settling tank being linked to the aeration tank.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

DETAILED DESCRIPTION OF THE PREFERRED EMBODIMENTS

The present invention provides a method of preparing a microbial culture for wastewater treatment comprising the steps of supplying an aerated material derived from an aeration tank to a bioreactor and cultivating a microorganism existing in the aerated material by adding a culture medium to the bioreactor.

Preferably, the culture medium comprises 0.05–3 wt % peptone, 0.01–2 wt % yeast extract, 0–2 wt % glucose, 0–2 wt % $KH_2PO_4$, 0–1 wt % $K_2HPO_4$, 0.001–0.1 wt % magnesium sulfate, and 0.0001–0.5 wt % iron chloride on the basis of the aerated material. Content of every component is a solid content on the basis of the weight of aerated material. The culture medium need not have water because of the aerated material is an aqueous solution. If the content of every component deviates from the range, pH of the medium, number and species of a microorganism can be change.

Figure 1:
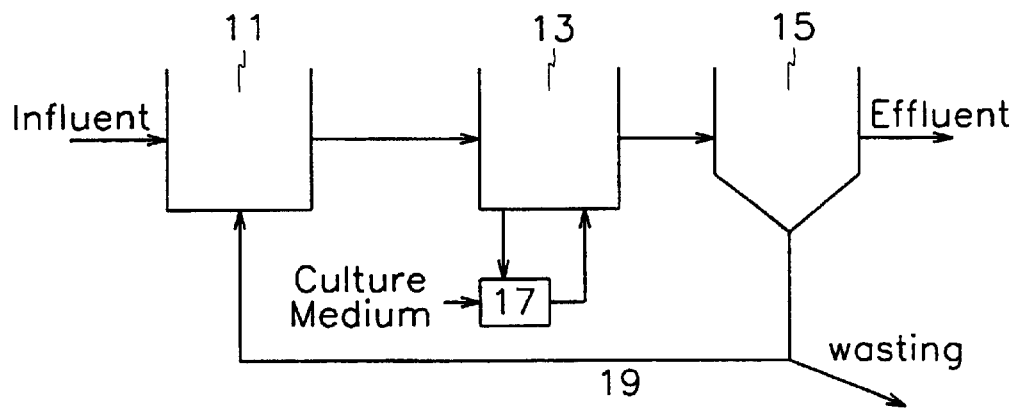
FIG. 1 is a schematic diagram of a wastewater treatment plant according to the present invention.
Figure 2:
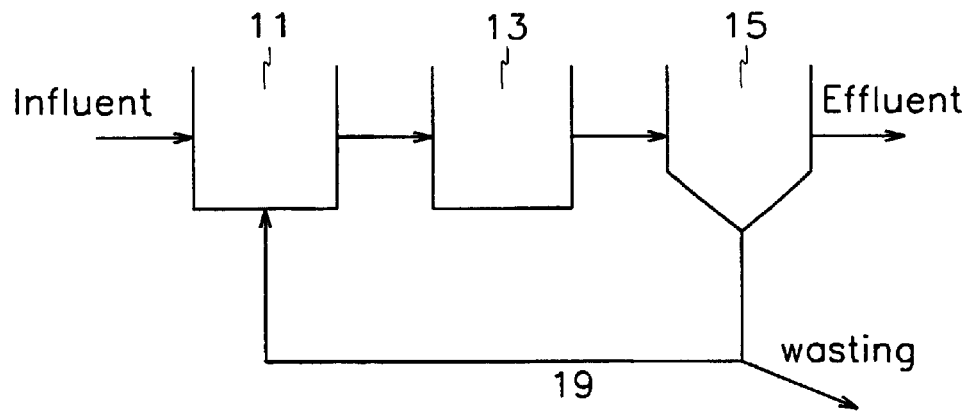
FIG. 2 is a schematic diagram of a wastewater treatment plant according to the conventional activated sludge process.

As shown in FIG. 1, the present invention provides a wastewater treatment plant comprising: a primary settling tank (11) for removing a solid substance and a suspended solid substance from a raw sewage; an aeration tank (13) for decomposing an organic material in a raw sewage by aerating the raw sewage with a microorganism, the aeration tank (13) being linked to the primary settling tank (11); a bioreactor (17) linked to the aeration tank (13), the bioreactor (17) being supplied with an aerated material from the aeration tank (13) and a culture medium, preparing a microbial culture by mixing the aerated material with the culture medium, and supplying the microbial culture to the aeration tank (13); and a secondary settling tank (15) for settling a sludge floc supplied from the aeration tank (13), the settling tank (15) being linked to the aeration tank (13).

Preferably, the culture medium comprises 0.05–3 wt % peptone, 0.01–2 wt % yeast extract, 0–2 wt % glucose, 0–2 wt % $KH_2PO_4$, 0–1 wt % $K_2HPO_4$, 0.001–0.1 wt % magnesium sulfate, and 0.0001–0.5 wt % iron chloride on the basis of the aerated material.

A microorganism having a relatively high activation to wastewater exists in the aeration tank of the wastewater treatment plant. In the present invention, a microorganism separated from the aeration tank is cultivated in a liquid medium and the microorganism is supplied to the aeration tank, thereby increasing a concentration of the microorganism having a high activation to wastewater in the aeration tank.

A state of microorganism is dependent on COD of the aeration tank. A microorganism separated from an aerated material including many organic materials, has a relatively high activation to wastewater. Therefore, it is preferable that the aerated material derived from the aeration tank is used as a seed to obtain a high activation microbial culture.

A composition of the medium can be variable according to species of microorganism. For example, the medium comprising 0.05–3 wt % peptone, 0.01–2 wt % yeast extract, 0–2 wt % glucose, 0–2 wt % $KH_2PO_4$, 0–1 wt % $K_2HPO_4$, 0.001–0.1 wt % magnesium sulfate, and 0.0001–0.5 wt % iron chloride may be used. When the medium has an excessive quantity of glucose as a carbon source, mold can be cultivated predominantly in the aeration tank. When the composition of the medium is not appropriate, number or type of the microorganism can be change. The medium may comprise a small quantity of mineral except for the carbon source and a buffer solution. The medium is favorable to separate an effective microorganism from the aeration tank compared to a nutrient medium because the composition of the medium is similar to the composition of a minimal medium.

EXAMPLE 1

A mixture of 0.3 wt % peptone, 0.05 wt % yeast extract, 0.02 wt % $KH_2PO_4$, 0.005 wt % magnesium sulfate and 0.0001 wt % iron chloride on the basis of an aerated material was sterilized by γ-ray radiation (10 KGY). The sterilized solid mixture and the aerated material were added to a bioreactor and cultivated for 24 hours at 30° C., wherein the aerated material had been derived from an aeration tank of a wastewater treatment plant of a polyester filament yarn manufacturing factory. A principal ingredient of the aerated material was ethylene glycol.

Comparative Example 1-1

A mixture of 2 wt % glucose, 0.1 wt % yeast extract, 0.2 wt % $K_2HPO_4$, 0.04 wt % magnesium sulfate and 0.7 wt % ammonium sulfate and 0.05 wt % iron chloride on the basis of an aerated material was sterilized by γ-ray radiation (10

KGY). The sterilized solid mixture and the aerated material were added to a bioreactor and cultivated for 24 hours at 30° C., wherein the aerated material had been derived from an aeration tank of a wastewater treatment plant of a polyester filament yarn manufacturing factory. A principal ingredient of the aerated material was ethylene glycol.

Comparative Example 1-2

A mixture of 2 wt % glucose, 0.1 wt % yeast extract, 0.2 wt % $K_2HPO_4$, 0.04 wt % magnesium sulfate and 0.7 wt % ammonium sulfate, 0.05 wt % iron chloride, 0.24 wt % $(NH_4)_3PO_4$ and 0.3 wt % $(NH_4)_2HPO_4$ on the basis of an aerated material was sterilized by γ-ray radiation (10 KGY). The sterilized solid mixture and the aerated material were added to a bioreactor and cultivated for 24 hours at 30° C., wherein the aerated material had been derived from an aeration tank of a wastewater treatment plant of a polyester filament yarn manufacturing factory. A principal ingredient of the aerated material was ethylene glycol.

Example 1 was not observed a growth of a mold or yeast compared to Comparative example 1-1 and Comparative example 1-2. Example 1 had a lot of species of microorganism compared to Comparative example 1-1 and Comparative example 1-2. Comparative example 1-1 and Comparative example 1-2 were observed a growth of a mold or yeast because of using glucose as a carbon source for a medium. Comparative example 1-2 including ammonium as the buffer solution was observed a pH decrease of the medium as time went by.

EXAMPLE 2

A solid medium was prepared by adding 1.7 wt % an agar to the liquid medium of Example 1. Example 1 was repeated except that the solid medium used as the medium.

Comparative Example 2

Example 1 was repeated except that a tryptic soy agar (Difco. Co.) was used as the medium.

Table 1 shows results of Example 2 and Comparative example 2.

TABLE 1

|  | Example 2 | Comparative example 2 |
| --- | --- | --- |
| Number of aerobic bacteria (CFU/ml) | $3.6 \times 10^7$ | $8 \times 10^5$ |
| Species of bacteria (species) | 9 | 6 |

Example 2 had a large number of aerobic bacteria and species of bacteria compared to Comparative example 2. The medium of Example 2 is favorable to cultivate microorganisms derived from the aeration tank compared to Comparative example 2. Number and species of the bacteria were dependent on the composition of the medium.

EXAMPLE 3

A microorganism derived from the aeration tank was cultivated in the liquid medium of Example 1. Number of a microorganism involved in ethylene glycol decomposition was measured by using a minimal medium comprising 0.05 wt % $NH_4Cl$, 0.05 wt % $(NH_2)_2SO_4$, 0.3 wt % $Na_2HPO_4$, 0.2 wt % $KH_2PO_4$, 0.001 wt % $MgSO_4$, 0.0001 wt % $FeCl_3$, and 1 wt % ethylene glycol. Number of the total effective microorganism was measured by using the solid medium of Example 2.

Comparative Example 3

Example 3 was repeated except that the microorganism derived from the aeration tank was not cultivated in the liquid medium of Example 1.

Table 2 shows results of Example 3 and Comparative example 3.

TABLE 2

|  | Example 3 | Comparative example 3 |
| --- | --- | --- |
| Number of effective microorganisms (CFU/ml) | $3 \times 10^{11}$ | $4 \times 10^6$ |
| Number of microorganism involved in ethylene glycol decomposition (CFU/ml) | $8 \times 10^7$ | $3 \times 10^4$ |

As shown in table 2, Example 3 had a large number of effective microorganism and a large number of microorganism involved in ethylene glycol decomposition compared to Comparative example 3.

EXAMPLE 4

The liquid medium of Example 1 was sterilized. The sterilized medium was added to 1 ml of wastewater derived from an aeration tank having ethylene glycol as a principal ingredient. And then, the obtained mixture was cultivated for 24 hours 30° C. The cultivated microorganisms were supplied to the aeration tank in the concentration of 500 ppm, and it was aerated for 3 days in the aeration tank. And then, COD of the aerated material in the aeration tank and a degree of floc formation were measured.

Comparative Example 4

Example 4 was repeated except that the cultivated microorganism was not supplied to the aeration tank.

Table 3 shows results of Example 4 and Comparative example 4.

TABLE 3

|  | COD of Example 4 (ppm) | COD of Comparative example 4 (ppm) |
| --- | --- | --- |
| 24 hours | 208 | 196 |
| 48 hours | 128 | 168 |
| 72 hours | 54 | 131 |

* Initial COD of wastewater: 300 ppm

As shown in table 3, COD of Example 4 was higher than Comparative example 4 after 24 hours because the cultivated microorganism of Example 4 decomposed organic materials in the wastewater and propagated using it. However, COD of Example 4 was decreased gradually. Example 4 had a relatively high treating efficiency compared to Comparative example 4. Example 4 was observed a floc formation within 48 hours. On the contrary, Comparative example 4 was observed a floc formation after 72 hours.

Example 5 and Comparative Example 5

Bulking sewage was supplied to a pilot scale (70L×4), wherein filamentous microorganisms were predominant in bulking sewage. A microbial culture was prepared by using the medium of Example 1 and an aerated material separated from an aeration tank of the pilot scale. The microbial culture was supplied to the aeration tank in the concentration of 500 ppm for 7 days.

Figure 3:
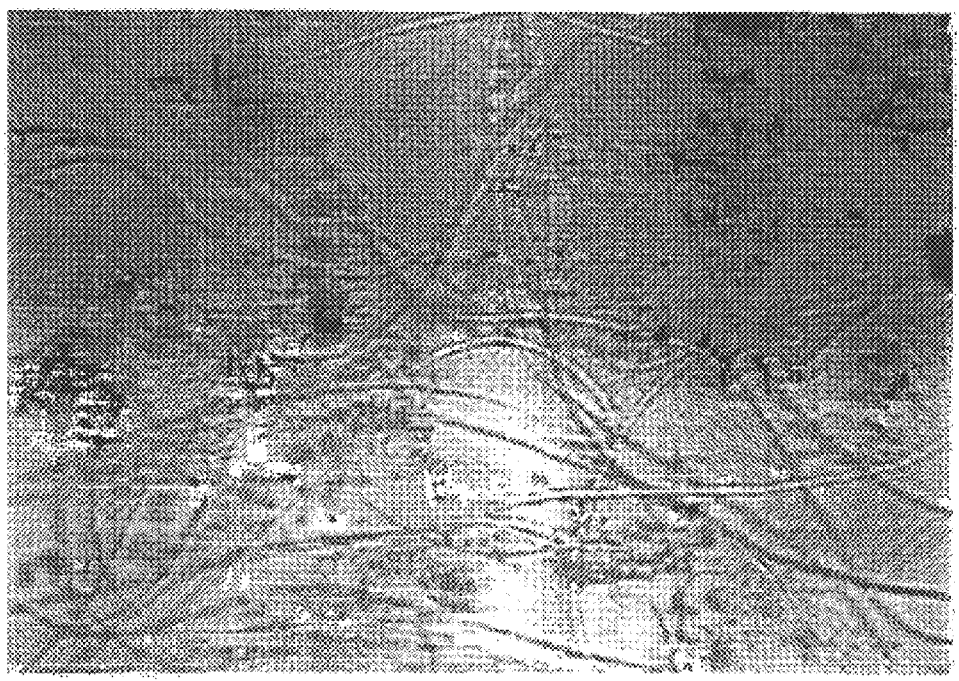
FIG. 3 is a photograph of microorganisms in the aeration tank before treating the microbial culture according to the present invention.

FIG. 3 is a photograph of microorganisms in the aeration tank before treating the microbial culture. As shown in FIG.

3, microorganisms involved in the floc formation were filamentous bacteria.

Figure 4:
FIG. 4 is a photograph of microorganisms in the aeration tank after 24 hours have passed since treating the microbial culture according to the present invention.

FIG. 4 is a photograph of microorganisms in the aeration tank after 24 hours have passed since treating the microbial culture. Although filamentous bacteria were observed in the floc, the floc was returned to a normal floc gradually. After 24 hours have passed since treating the microbial culture, a shape of the floc was similar to bulking sewage. However, number of nonfilamentous bacteria was increased.

Figure 5:
FIG. 5 is a photograph of microorganisms in the aeration tank after 48 hours have passed since treating the microbial culture according to the present invention.

FIG. 5 is a photograph of microorganisms in the aeration tank after 48 hours have passed since treating the microbial culture. Although filamentous bacteria were observed in the floc, the floe was returned to a normal floc gradually.

Figure 6:
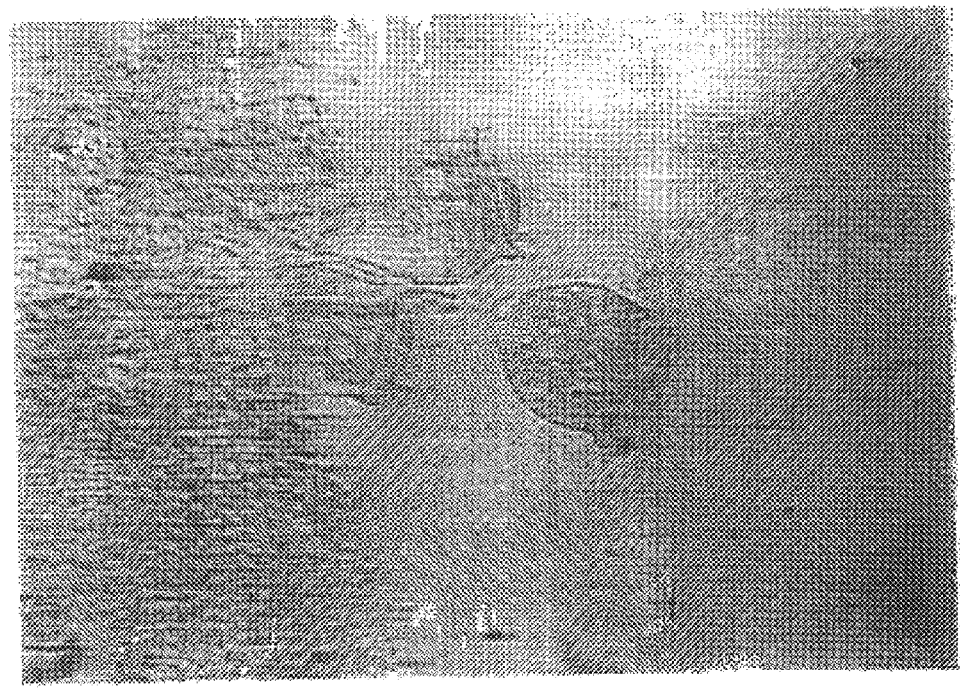
FIG. 6 is a photograph of microorganisms in the aeration tank after 72 hours have passed since treating the microbial culture according to the present invention.

FIG. 6 is a photograph of microorganisms in the aeration tank after 72 hours have passed since treating the microbial culture. The floc was returned to a normal floc gradually. After 72 hours have passed since treating the microbial culture, filamentous bacteria of the aeration tank were replaced by nonfilamentous bacteria.

Figure 7:
FIG. 7 is a photograph of the state of microorganism in the aeration tank after 168 hours have passed since treating the microbial culture according to the present invention.

FIG. 7 is a photograph of the state of microorganism in the aeration tank after 168 hours have passed since treating the microbial culture. As shown in FIG. 7, filamentous bacteria were not observed in the floc and protozoa such as Vorticella spp. and Aspidisca spp. was observed in the floc. The microbial culture according to the present invention can return the floc to a normal floc. In the process of cultivating effective microorganisms derived from the aeration tank, nonfilamentous bacteria, not filamentous bacteria, may be cultivated predominantly.

The microbial culture includes microorganism adapted to the aeration tank environment. Therefore, the present invention can omit an activation process to adapt the microbial culture to the aeration tank. The microbial culture has a relatively high organic material decomposition ability compared to the conventional microbial culture. The microbial culture has a relatively high preservation time and treating efficiency.

Every wastewater treatment plant includes characteristic organic material. A microorganism well-adapted to the organic material exits in an aeration tank of the plant. The microbial culture of the present invention was prepared by using the microorganism derived from the aeration tank. Therefore, the present invention provides a microbial culture having a relatively high treating efficiency compared to the conventional microbial culture having the microorganism separated from nature such as soil.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A wastewater treatment plant comprising:
    a primary settling tank for removing a solid substance and a suspended solid substance from a raw sewage;
    an aeration tank for decomposing an organic material in a raw sewage by aerating the raw sewage with a microorganism, the aeration tank being linked to the primary settling tank;
    a bioreactor linked to the aeration tank, the bioreactor being supplied with an aerated material form the aeration tank and a supplementary culture medium, wherein the aerated material comprises a plurality of different microorganisms, preparing a microbial culture by mixing the aerated material with the culture medium, and supplying the microbial culture including the plurality of different microorganisms to the aeration tank; and
    a secondary settling tank for settling tank for settling a sludge floc supplied from the aeration tank, the settling tank being linked to the aeration tank.

2. The wastewater treatment plant of claim 1, wherein the medium comprises 0.05–3 wt % peptone, 0.01–2 wt % yeast extract, 0–2 wt % glucose, 0–2 wt % $KH_2PO_4$, 0–1 wt % $K_2HPO_4$, 0.001–0.1 wt % magnesium sulfate, and 0.0001–0.5 wt % iron chloride on the basis of the aerated material.

* * * * *